(12) United States Patent
Pistor et al.

(10) Patent No.: US 9,737,199 B2
(45) Date of Patent: Aug. 22, 2017

(54) ROBOTIC LINKAGE

(71) Applicant: INTUITIVE SURGICAL OPERATIONS, INC., Sunnyvale, CA (US)

(72) Inventors: Christoph Matthias Pistor, Santa Cruz, CA (US); Joshua T Oen, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/172,127

(22) Filed: Jun. 2, 2016

(65) Prior Publication Data
US 2017/0000315 A1    Jan. 5, 2017

Related U.S. Application Data

(63) Continuation of application No. 12/615,941, filed on Nov. 10, 2009, which is a continuation-in-part of
(Continued)

(51) Int. Cl.
*B25J 17/00* (2006.01)
*B25J 18/00* (2006.01)
(Continued)

(52) U.S. Cl.
CPC ............ *A61B 1/0055* (2013.01); *A61B 34/30* (2016.02); *B25J 18/06* (2013.01); *A61B 2034/301* (2016.02); *Y10T 74/20329* (2015.01)

(58) Field of Classification Search
CPC ...... A61B 1/0055; A61B 34/30; B25J 9/0012; B25J 18/06
See application file for complete search history.

(56) References Cited

U.S. PATENT DOCUMENTS 616,672 A    12/1898 Kelling
2,510,198 A   6/1950 Tesmer
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Terence Boes
(74) *Attorney, Agent, or Firm* — Jones Robb, PLLC

(57) ABSTRACT

A method may include articulating a first link and a second link relative to each other about a pair of outer hinge portions on a first end of a first link and in mating engagement with a pair of inner hinge portions on a second end of a second link. Each outer hinge portion comprises an outer ear extending in a first axial direction away from the first end of the first link, and an inner bearing surface substantially oriented in the first axial direction, and each inner hinge portion comprises an inner ear extending in a second axial direction away from the second end of the second link, and an outer bearing surface positioned oriented in the second axial direction. During the articulating, the outer bearing surfaces support the outer ears and the inner bearing surfaces support the inner ears.

20 Claims, 14 Drawing Sheets
(1 of 14 Drawing Sheet(s) Filed in Color)

Related U.S. Application Data application No. 12/615,897, filed on Nov. 10, 2009, now abandoned.

(60) Provisional application No. 61/113,453, filed on Nov. 11, 2008.

(51) Int. Cl.
*B29C 41/42* (2006.01)
*A61B 1/005* (2006.01)
*B25J 18/06* (2006.01)
*A61B 34/30* (2016.01)

(56) References Cited

U.S. PATENT DOCUMENTS

| | | |
|---|---|---|
| 3,060,972 A | 10/1962 | Sheldon |
| 3,190,286 A | 6/1965 | Stokes |
| 3,266,059 A | 8/1966 | Stelle |
| 3,270,641 A | 9/1966 | Gosselin |
| 3,456,514 A | 7/1969 | Gebendinger |
| 3,497,083 A | 2/1970 | Anderson et al. |
| 3,557,780 A | 1/1971 | Sato |
| 4,347,837 A | 9/1982 | Hosono |
| 4,686,963 A * | 8/1987 | Cohen ............ A61B 1/0055 138/120 |
| 4,834,069 A | 5/1989 | Umeda |
| 5,174,277 A | 12/1992 | Matsumaru |
| 5,178,129 A | 1/1993 | Chikama et al. |
| 5,448,989 A | 9/1995 | Heckele |
| 5,624,380 A | 4/1997 | Takayama et al. |
| 6,817,974 B2 * | 11/2004 | Cooper ........ A61B 17/00234 600/142 |
| 2004/0138525 A1 | 7/2004 | Saadat et al. |
| 2005/0197536 A1 * | 9/2005 | Banik ............ A61B 1/00059 600/179 |
| 2005/0250990 A1 * | 11/2005 | Le ................ A61B 1/00135 600/114 |
| 2009/0099420 A1 | 4/2009 | Woodley et al. |
| 2009/0216083 A1 | 8/2009 | Durant et al. |
| 2010/0116080 A1 | 5/2010 | Pistor et al. |
| 2010/0116081 A1 | 5/2010 | Pistor et al. |

\* cited by examiner

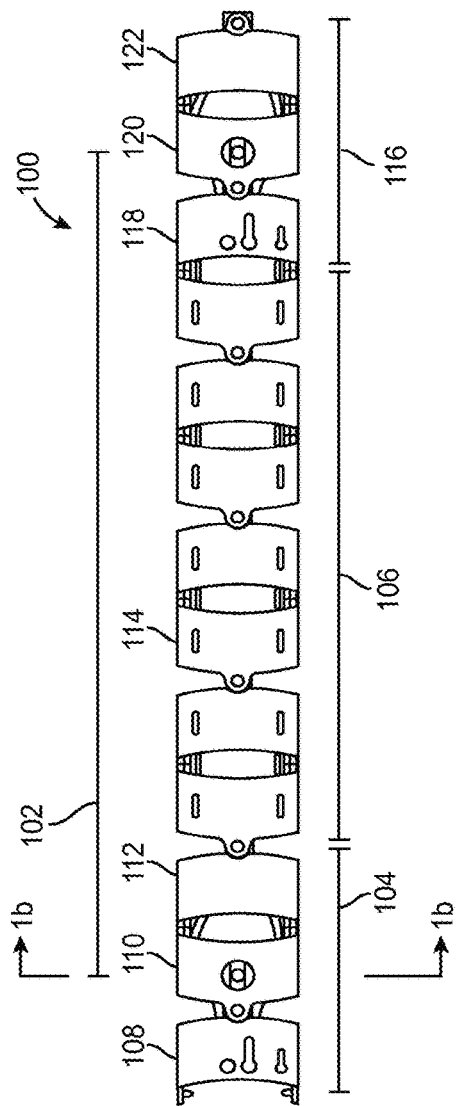
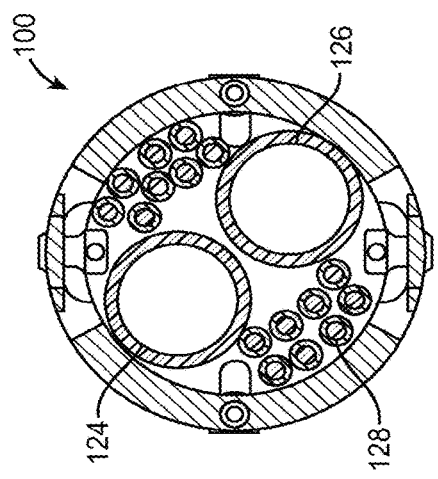
FIG. 1a
FIG. 1b

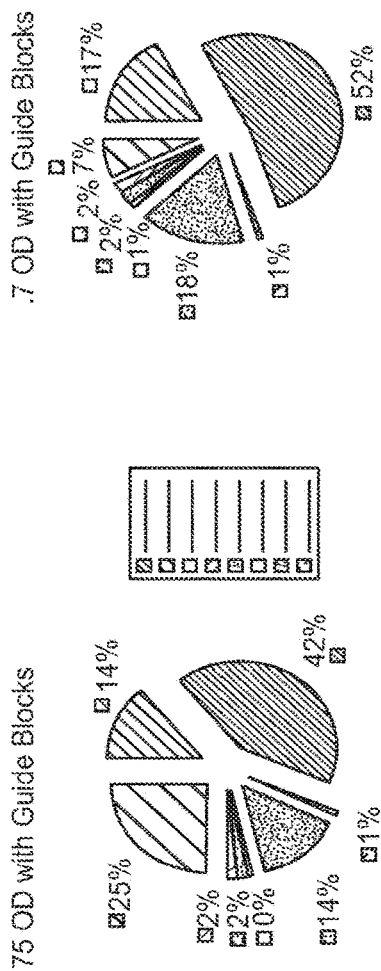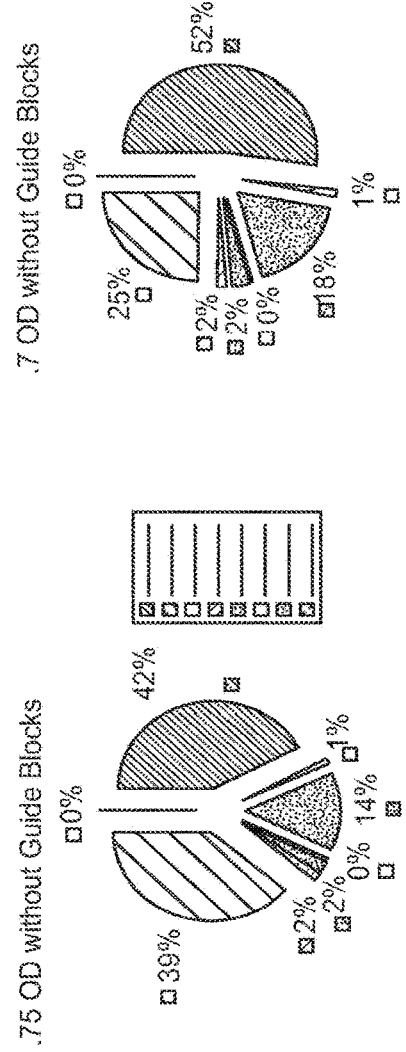

ROBOTIC LINKAGE

This application is a continuation application of U.S. application Ser. No. 12/615,941 (filed Nov. 10, 2009; titled "ROBOTIC LINKAGE"), which is a continuation-in-part of U.S. application Ser. No. 12/615,897 (filed Nov. 10, 2009; titled "ROBOTIC LINKAGE"), and which claims the benefit under 35 U.S.C. 119 of U.S. Patent Application No. 61/113,453 (filed Nov. 11, 2008; titled "ROBOTIC LINKAGE"), each of which is incorporated herein by reference.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF INVENTION

The present invention relates generally to elongate robotic instruments and elongate surgical robots, such as robotic endoscopes. More particularly, it relates to methods and apparatuses for manufacturing and forming elongate robotic instruments.

BACKGROUND

The forms of elongate robotic instruments vary widely, but many elongate robotic instruments share the features of a mechanical, movable structure under some form of control. The mechanical structure or kinematic chain (analogous to the human skeleton) of an elongate robotic instrument can be formed from several links (analogous to human bones), actuators (analogous to human muscle), and joints between the links, permitting one or more degrees of freedom of motion of the links. A continuum or multi-segment elongate robotic instrument can be a continuously curving device, like an elephant trunk for example. An example of a continuum or multi-segment elongate robotic instrument is a snake-like endoscopic device.

Snake-like endoscopic devices can transfer forces from an actuator to particular sections of links in the snake-like device to effect articulation of that section or link. During articulation, these links are subjected to large stresses that can result in breakage or failure of the link and thus, failure of the endoscopic device. These failures typically occur at the weak point between links, such as at the joints.

A typical robotic link is made from a metal or alloy, such as aluminum or stainless steel. The links can be manufactured by laser cutting tubes, by laser sintering, by metal injection molding, or other processes as known in the art. Furthermore, a snake-like endoscopic device can often include several types of links, such as distal and proximal links for attachment to actuators, and intermediate links therebetween. However, manufacturing elongate robotic devices with these materials, as well as needing several different types of links for each device, can be expensive and add to the cost of an elongate robotic instrument.

An elongate robotic instrument, and more particularly a link that is used to make up the elongate robotic instrument, is therefore needed that can be manufactured efficiently and inexpensively while still being able to withstand the stresses imposed upon it during normal use.

SUMMARY

In one embodiment, a robotic link is provided comprising a link having an outer wall surface and an inner wall surface, a pair of outer hinge portions on a first end of the link, each outer hinge portion having an inner bearing surface positioned between the inner wall surface and an outer ear, and a pair of inner hinge portions on a second end of the link, each inner hinge portion having an outer bearing surface positioned between the outer wall surface and an inner ear.

In some embodiments, the robotic link comprises a polymer. The robotic link can comprise PEEK, for example.

In one embodiment, each of the pair of outer hinge portions are diametrically opposed across the link. In another embodiment, each of the pair of inner hinge portions are diametrically opposed across the link. In some embodiments, an axis of rotation of the outer hinge portions are substantially perpendicular to an axis of rotation of the inner hinge portions.

The robotic link can further comprise a guide block positioned along each inner and outer hinge portion. In some embodiments, a tendon guide is positioned integrally within the link along each inner and outer hinge portion. The robotic link can also comprise an integrated pulley and tendon guide positioned integrally within the link along each outer hinge portion. In some embodiments, the robotic link comprises an integrated pulley and tendon guide positioned integrally within the link along each inner and outer hinge portion.

In one embodiment, the robotic link has an outer diameter of less than or equal to 19.05 millimeters (0.75 inches).

A flexible robotic instrument is provided, comprising a first link and a second link each having an outer wall surface and an inner wall surface, a pair of outer hinge portions disposed on a first end of each link, each outer hinge portion having an inner bearing surface positioned between the inner wall surface and an outer ear of each link, and a pair of inner hinge portions on a second end of each link, each inner hinge portion having an outer bearing surface positioned between the outer wall surface and an inner ear of each link, wherein the outer bearing surface of the first link is configured to slidably support the outer ear of the second link, and wherein the inner bearing surface of the second link is configured to slidably support the inner ear of the first link.

In some embodiments, the first and second links comprise a polymer. The first and second links can comprise PEEK, for example.

In one embodiment, an interior volume of the instrument is sized to accommodate at least two working channels.

In some embodiments, each of the pair of outer hinge portions are diametrically opposed across the first and second links. Similarly, each of the pair of inner hinge portions can be diametrically opposed across first and second links. In one embodiment, the outer hinge portions are substantially perpendicular to the inner hinge portions.

The flexible robotic instrument can further comprise a guide block positioned along each inner and outer hinge portion. In some embodiments, a tendon guide is positioned integrally within the first and second links along each inner and outer hinge portion. In other embodiments, the flexible robotic instrument can comprise an integrated pulley and tendon guide positioned integrally within the first and second links along each inner and/or outer hinge portion.

In one embodiment, the flexible robotic instrument has an outer diameter of less than or equal to 19.05 millimeters (0.75 inches).

The flexible robotic instrument can further comprise a plurality of actuation tendons.

In one embodiment, the first and second link of the flexible robotic instrument can articulate up to approximately +/−30 degrees individually.

A method of manufacturing a robotic link is provided, comprising introducing a polymer into a mold, and recovering from the mold a link having an outer wall surface and an inner wall surface, a pair of outer hinge portions on a first end of the link, each outer hinge portion having an inner bearing surface positioned between the inner wall surface and an outer ear, the link also having a pair of inner hinge portions on a second end of the link, each inner hinge portion having an outer bearing surface positioned between the outer wall surface and an inner ear.

BRIEF DESCRIPTION OF THE DRAWINGS

The patent or application file contains at least one drawing executed in color. Copies of this patent or patent application with color drawing(s) will be provided by the Office upon request and payment of the necessary fee.

FIGS. 1a-1b are illustrations of an elongate robotic instrument.

FIGS. 11a-11d are schematic illustrations showing the effect of guide blocks within a link and vertebra diameter on dead space.

DETAILED DESCRIPTION OF THE INVENTION

Figure 2:
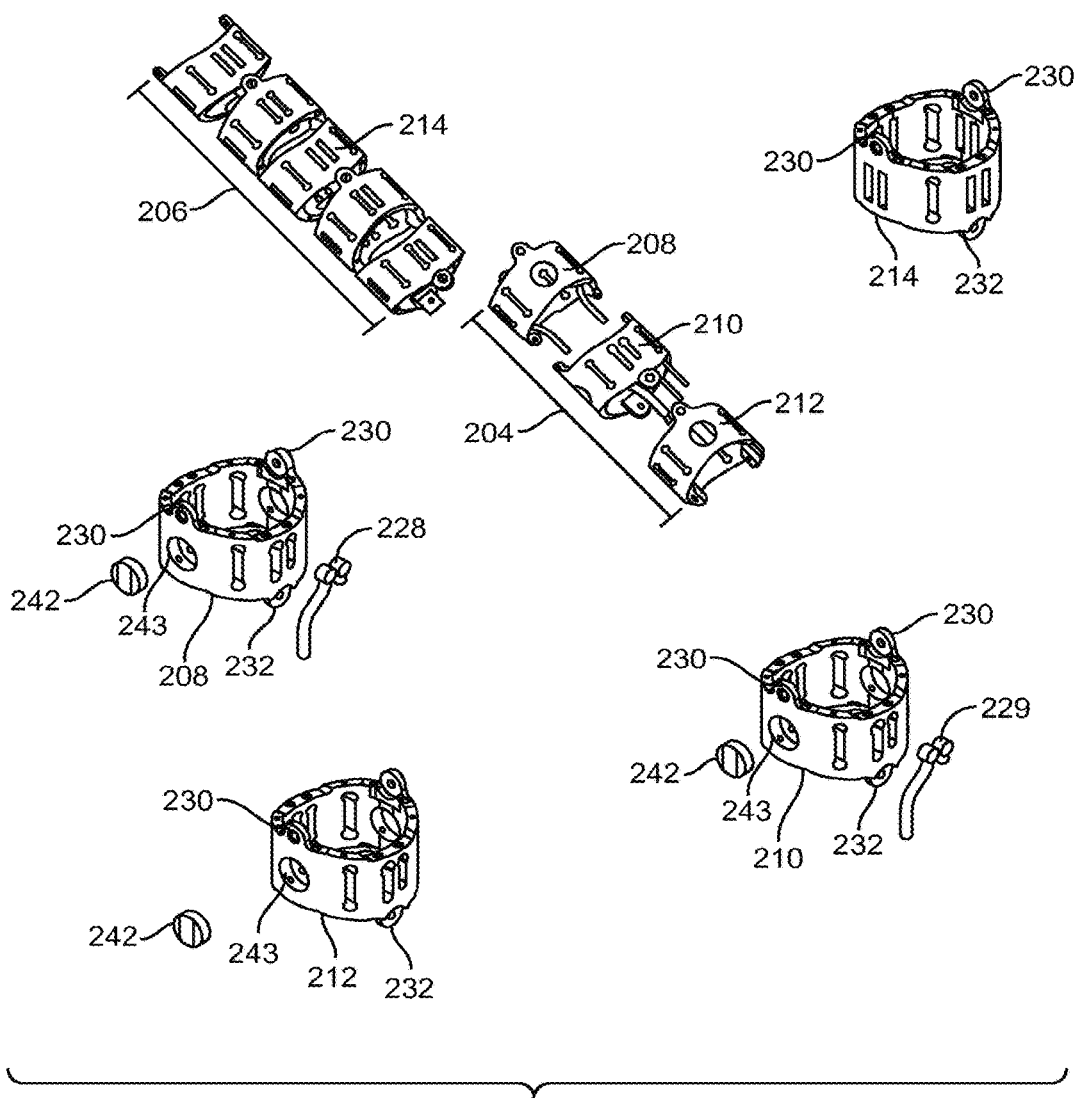
FIG. 2 is an exploded view of the elongate robotic instrument of FIGS. 1a-1b.

FIG. 1a is a side view of an elongate robotic instrument 100 comprising at least one individually articulatable segment 102. The elongate robotic instrument can comprise any number of articulatable segments, depending on the desired length of the instrument. One embodiment includes four such articulatable segments. As shown in FIG. 1a, the instrument includes a distal (farther from the base) boundary portion 104, an intermediate portion 106, and a proximal boundary portion 116. As shown in FIG. 1a, the boundary portions includes front links 108 and 118, middle links 110 and 120, and back links 112 and 122, and the intermediate portion includes multiple intermediate links 114. In FIG. 1a, the segment 102 extends from the middle of boundary portion 104 (i.e., the middle of link 110) to the middle of boundary portion 116 (i.e., the middle of link 120). The embodiment of FIG. 1a includes a total of seven intermediate links per segment, but in other embodiments various numbers of intermediate links can be used.

As will be described in more detail below, the front link 108 and middle link 110 are manufactured to provide features for coil tube and actuation tendon terminations, and the middle link 110 and back link 112 are manufactured to provide pulley features for the coil tubes and actuation tendons.

FIG. 1b is a cross sectional view of instrument 100 of FIG. 1a. It can be seen that instrument 100 provides room for at least two working channels or lumens 124 and 126. These working lumens can house various components, such as air and water channels, vacuum channels, fiber optic illumination light bundles, an imaging system (e.g., a fiber optic imaging system), surgical tools, and/or position and orientation sensors (e.g., electromagnetic sensors (such as those made by the Ascension company), accelerometers, etc). In some embodiments, position and orientation sensors can be placed in other portions of the instrument, such as along the inner or outer wall of the instrument. The working lumens generally extend through the length of the instrument 100. Generally, a user views live or delayed video feed from the imaging system via a video cable (e.g., wire or optical fiber, not shown) or through wireless transmission of the video signal. These channels and other amenities are shown generically, because such channels and amenities are well known in the art. The instrument 100 further includes actuation tendons 128 for changing the shape of the robotic instrument. The actuation tendons can be housed in coil tubes to provide additional strength and protection for the tendons, for example. In one embodiment the tendons are made from ultra high molecular weight polyethylene (UH-MWP). In some embodiments, the actuation tendons can run straight through the robotic instrument. In other embodiments, the actuation tendons can be helixed through the robotic instrument. In one embodiment, the steerable portion of each segment in the robotic instrument utilizes four actuation tendons for movement. Thus, an instrument having four steerable segments would require sixteen actuation tendons to achieve the full range of motion.

FIG. 2 is an exploded view of robotic links that can make up a robotic instrument, similar to the robotic instrument 100 of FIGS. 1a-1b. As shown in FIG. 2, distal boundary portion 204 includes front link 208, middle link 210, and back link 212. Intermediate portion 206 comprises a plurality of intermediate links 214. Not shown in FIG. 2 is the proximal boundary portion (similar to proximal boundary portion 116 in FIG. 1). The instrument 100 of FIG. 1a included seven intermediate links per segment plus 1.5 links from each boundary portion for a total of ten links, whereas the instrument shown in FIG. 2 includes only five intermediate links per segment plus 1.5 links from each boundary portion, for a total of eight links. If each pair of links is capable of articulating approximately +/−30 degrees individually, for example, then each segment of FIG. 1a can articulate 150 degrees, and each segment of FIG. 2 can articulate 120 degrees. Front link 208 may provide a termination point for a first pair of actuation tendons 228 and/or coil tubes. Middle link 210 may provide a termination point for a second pair of actuation tendons 229 and/or coil tubes. In another embodiment described below, the tendons may alternatively engage the front and middle links at pulley wheels 242, which are sized to fit within pulley slots 243 in the middle and back links. As will also be described in more detail below, pulling on one of the first pair of actuation tendons can cause a segment of the robotic instrument to move in a first plane (e.g., the X-plane), and pulling on one of the second pair of actuation tendons can cause the segment to move in a second plane (e.g., the Y-plane).

In order to reduce manufacturing costs, various implementations of the robotic links described herein can be made of a plastic or polymer. In one embodiment, the robotic links are polyaryletheretherketone (PEEK). The robotic links can be formed or manufactured by injection molding a polymer into a mold and then recovering a link from the mold, or by other methods as known in the art. The mold can be preformed to provide a link having any or all of the features described herein.

It can be seen in FIG. 2 that each link, including front link 208, middle link 210, back link 212, and intermediate links 214, comprises a pair of outer hinge portions 230 and a pair of inner hinge portions 232. The pair of outer hinge portions can be positioned substantially perpendicular to the pair of inner hinge portions (e.g., a line running through the pair of outer hinge portions is substantially perpendicular to a line running through the pair of inner hinge portions). Staggering the pairs of hinges in substantially perpendicular planes allows each link to move at the hinges with one degree of freedom relative to an adjacent link. Three connected links results in a serial kinematic chain having two degrees of freedom. Thus, the joint between the first and second links in a segment can move within a first plane, while the joint between the second and third links in a segment can move within a second plane that is substantially perpendicular to the first plane. In one embodiment, the joint between two adjacent links can articulate approximately 30 degrees (e.g., +−0.30 degrees) in either direction with respect to one another. Furthermore, in one embodiment, a pair of adjacent links can have a length of approximately 27.94 millimeters (1.1 inches).

Figure 3A:
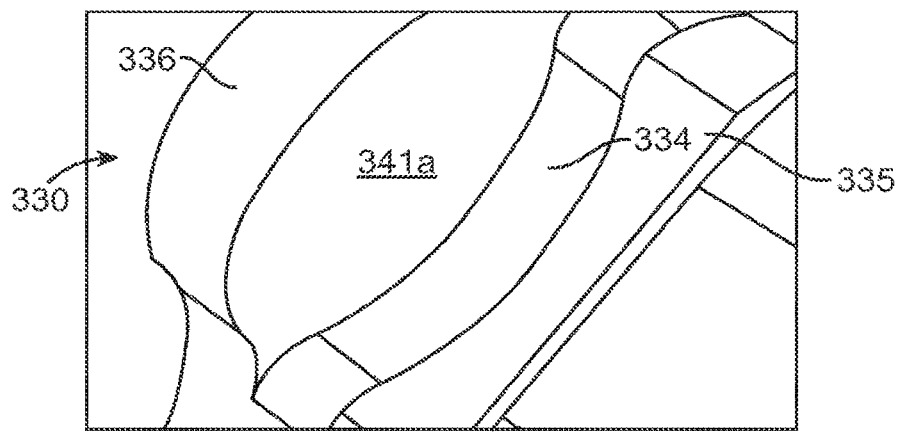
FIGS. 3a-3b illustrate a double-knee-joint of a robotic link.
Figure 3B:
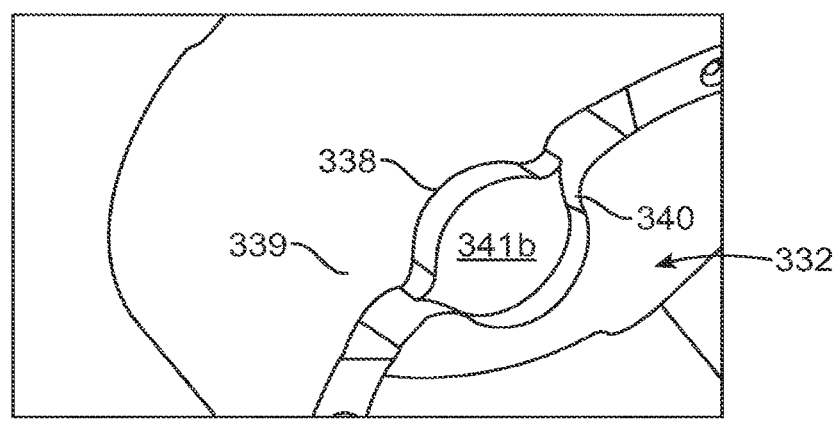

FIGS. 3a-3b illustrate zoomed-in perspective views of the outer and inner hinge portions of each robotic link (hinge pin holes are omitted from the drawings). As can be seen in FIG. 3a, outer hinge portion 330 includes an inner bearing surface 334 and an outer ear 336. Similarly, in FIG. 3b, inner hinge portion 332 includes an outer bearing surface 338 and an inner ear 340. As shown in FIGS. 3a-3b, each outer hinge portion 330 has an inner bearing surface 334 positioned between an inner wall surface 335 of the link and the outer ear 336. Similarly, each inner hinge portion 332 has an outer bearing surface 338 positioned between an outer wall surface 339 and the inner ear 340. It should be understood that the outer hinge portions 330 can be on a distal end of each link, and the inner hinge portions 332 can be on a proximal end of each link, as shown in FIG. 2. Alternatively, the outer hinge portions 330 can be on a proximal end of each link, and the inner hinge portions 332 can be on a distal end of each link (not shown).

When the inner hinge portion of one robotic link is joined to the outer hinge portion of another robotic link, the outer ear 336 rests in and is supported by the outer bearing surface 338, and the inner ear 340 rests in and is supported by the inner bearing surface 334. In some embodiments, the inner and outer bearing surfaces 334 and 338 are cup shaped or curved bearing surfaces, and the outer and inner ears 336 and 340 are sized to fit flush within and against their respective mating bearing surfaces, thus minimizing friction between each ear and bearing surface while maximizing the strength of the joint. Furthermore, the outside surface 341b of the inner ear of one link can be in slidable contact with the inside surface 341a of the outer ear of a mated link, which provides additional support to strengthen the joint formed when two links are coupled.

This inner/outer hinge portion configuration allows the distal pair of hinges of a first link to engage with the proximal pair of hinges of a second link. Each adjacent link can then be coupled to the next at the hinges to form a pivot joint, such as by inserting a pin, rivet, etc, through a hole in the hinges, for example. It should be understood that when the inner hinge portion of a one link is coupled to the outer hinge portion of another link, a rivet or other fixation device (not shown) can additionally secure the hinge portions together. When two links are mated in this way, the inner and outer ears slide on their associated bearing surfaces, which provides an effective load distribution when the links are axially compressed (e.g., such an axial load is not solely borne by hinge pins that hold the two links together). In addition, the sliding mated inner and outer hinge portions provide effective lateral load capacity.

When the inner and outer hinge portions pictured in FIGS. 3a-3b are joined together, the joint can be referred to as a "double-knee-joint." The double-knee-joint minimizes stress on the hinges when adjacent robotic links are coupled together and subjected to the forces consistent with actuation and movement of a robotic instrument. By strengthening the formerly weak point of actuation between adjacent links with this double-knee-joint design, the robotic links of the present invention can thus be manufactured from a polymer, such as PEEK, to reduce cost and improve ease of manufacturing.

Figure 4A:
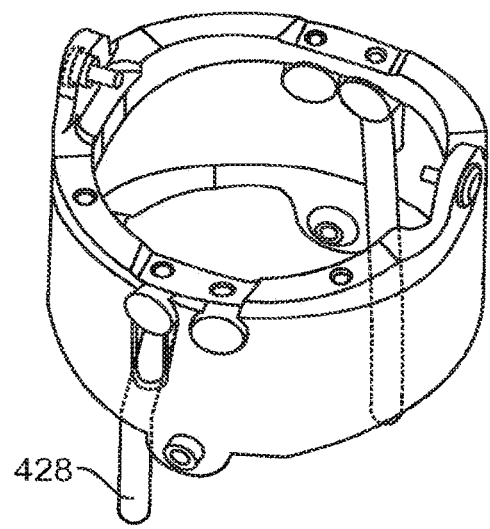
FIGS. 4a-4b are illustrations some embodiments of attachment points of actuation tendons and coil tubes in a robotic link.
Figure 4B:
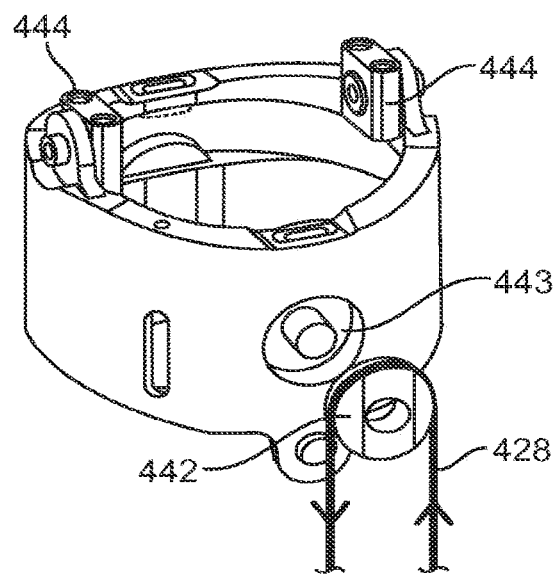

FIGS. 4a-4b illustrate two embodiments of terminating pairs of actuation tendons at their respective robotic links. Referring back to FIG. 2, it should be understood that actuation tendons are typically terminated at only the front link 208 and middle link 210 of the proximal boundary links of each segment (e.g., to provide x- and y-axis steering for the segment). In the embodiment shown in FIG. 4a, each actuation tendon 428 housed in a coil tube can terminate at or connect to a single point in the link, such as by crimping, glue, soldering, etc. However, in the embodiment shown in FIG. 4b, each actuation tendon 428 can wrap around pulley wheel 442 and be directed back towards the proximal end of the instrument (as shown by the arrows in actuation tendon 428). Pulley wheels 442 can be discrete mechanical pulleys sized to fit within pulley slots 443 in the sidewalls of each link. Using pulleys as a termination point for the actuation tendons causes a modification of the amount of force (mechanical advantage) applied to each segment when the tendons are actuated (e.g., pulled). The pulley provides a decrease in the distal force required to actuate a segment, at the cost of increased distal displacement. Eliminating the pulley requires a greater distal force for actuation but decreases the cable displacement required.

In operation, pulling each of the respective actuation tendons will increase the tension in the pulled tendon and cause the segment to articulate in the direction of the pulled tendon as the links articulate at their respective hinges. Additionally, when one tendon is tensioned, the opposite tendon in the segment can be slacked to accommodate movement of the segment, especially the tendon positioned 180 degrees or opposite from the tensioned tendon.

FIG. 4b also illustrates a robotic link having guide blocks 444 positioned along each inner hinge portion (guide blocks can be positioned along both the outer and inner hinge portions, not shown in FIG. 4b). The guide blocks can include a pair of lumens, as shown, for receiving actuation tendons. The guide blocks act as tendon guides and function to position the actuation tendons along each hinge. This causes the distance between the hinge and the off-axis cables to be reduced, and minimizes out-of-plane motion when a pair of cables is actuated.

In the illustrative link embodiments shown and described above, the same interchangeable link design can be used for both the boundary and intermediate portions of a segment. Thus, manufacturing costs are further reduced by eliminating the need for different link designs, and so using a single design that can be inexpensively manufactured by, e.g., injection molding, for all links in the kinematic chain. Various other link designs may also be used.

Figure 5A:
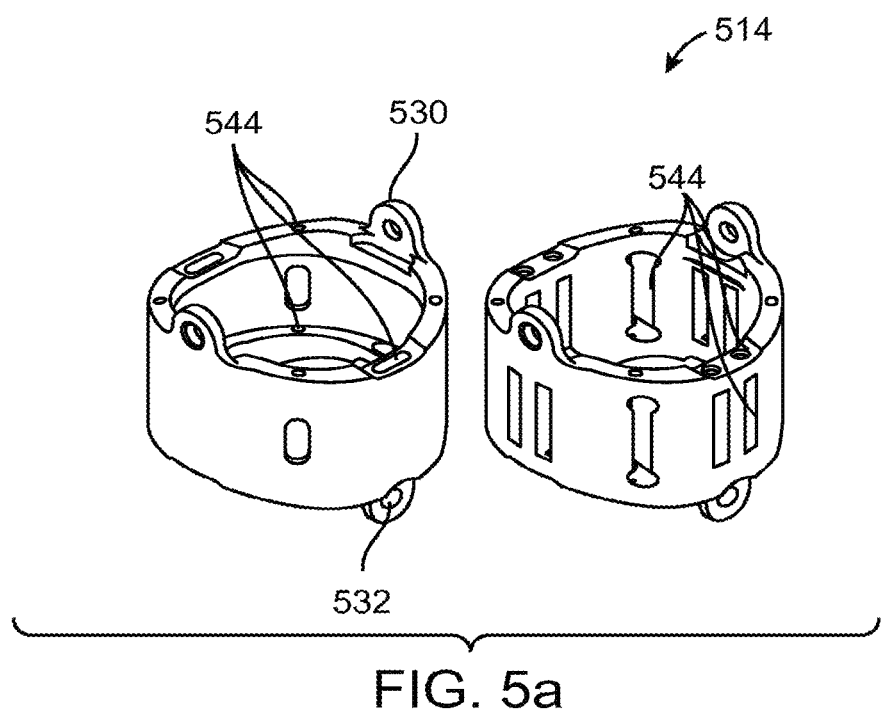
FIGS. 5a-5c are illustrations of various embodiments of robotic links.
Figure 5B:
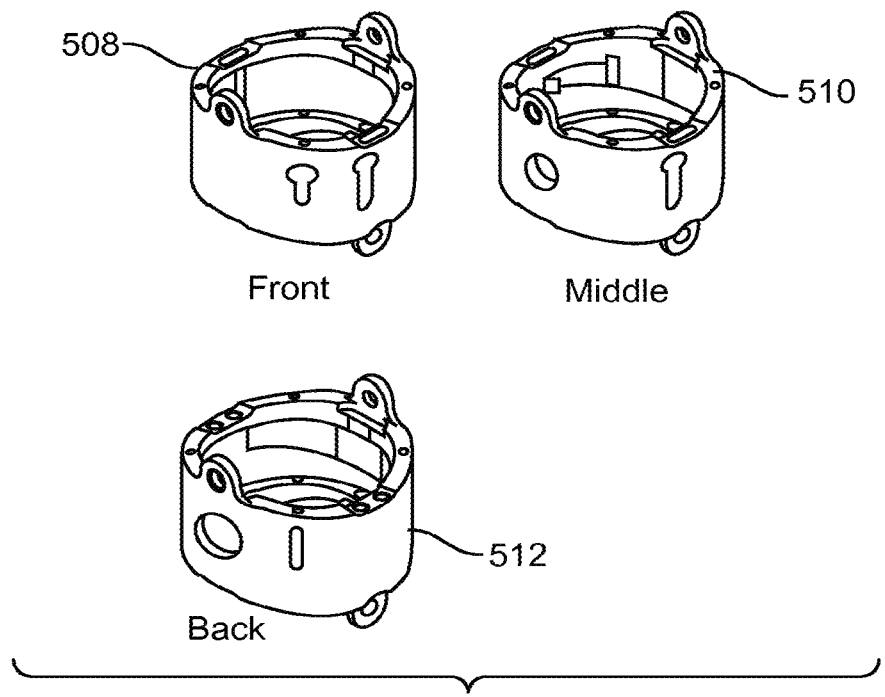

FIG. 5a illustrates another embodiment of intermediate links 514, and FIG. 5b illustrates another embodiment of front link 508, middle link 510, and back link 512 for use in an elongate robotic instrument. The links shown in FIGS. 5a-5b can include many of the features described above in FIGS. 1-4. For example, outer hinge portions 530 and inner hinge portions 532 can correspond, respectively, to outer hinge portions 230 and inner hinge portions 232 of FIG. 2. In addition, the guide blocks 444 described in FIGS. 4a-4b have now been incorporated into the body of the robotic link itself as an integrated tendon guides 544. As can be seen in FIG. 5a, actuation tendon guides 544 comprise a plurality of lumens integrally formed into the wall of each robotic link. The actuation tendons (not shown) can be routed through tendon guides 544 to provide the same function as the guide blocks described above (i.e., to keep the actuation tendons positioned along the hinges in each link).

Figure 5C:
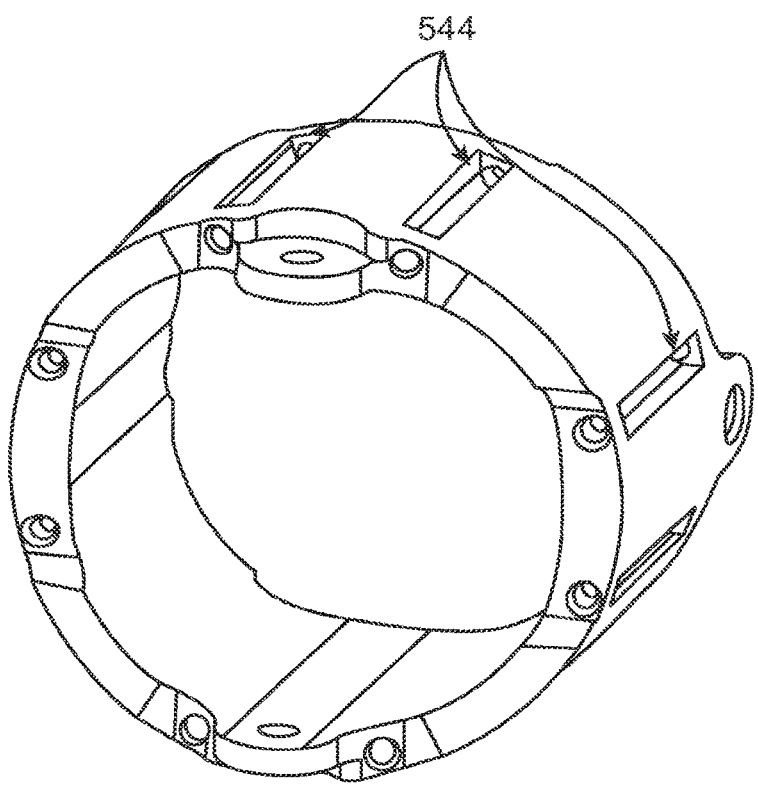

This design has the additional advantages of saving costs by reducing the number of parts, simplifying assembly, increasing available lumen/working channel volume within the robotic instrument, allowing helixed actuation tendons (if helixed) to propagate during assembly more easily, and avoiding restriction of local slack of the helixed tendons during articulation. FIG. 5c illustrates another view of actuation tendon guides 544 incorporated into the walls of the robotic links. It can be seen from FIG. 5c that the actuation tendon guides include at least two lumens per hinge portion per link. So in the link illustrated in FIG. 5c having four hinges, the tendon guides include eight lumens.

Figure 6:
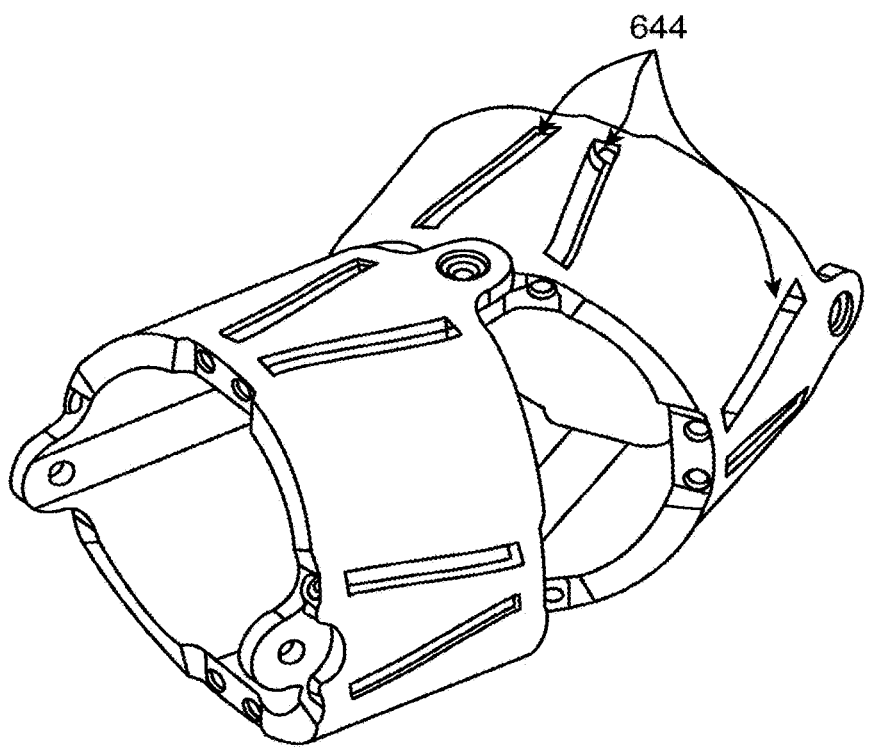
FIG. 6 is an illustration of another embodiment of a robotic link for use in an elongate robotic instrument.

FIG. 6 is another embodiment of a robotic link having actuation tendon guides 644 incorporated into the wall of the link. The embodiment of FIG. 6 is similar to that described above with respect to FIG. 5a, however the lumens of tendon guides 644 are incorporated at an angle with respect to the hinge instead of running parallel with the robotic instrument. The angled tendon guides allow the maximum articulation radius (lever arm) while still avoiding the hinge, at the cost of added friction in the instrument.

Figure 7A:
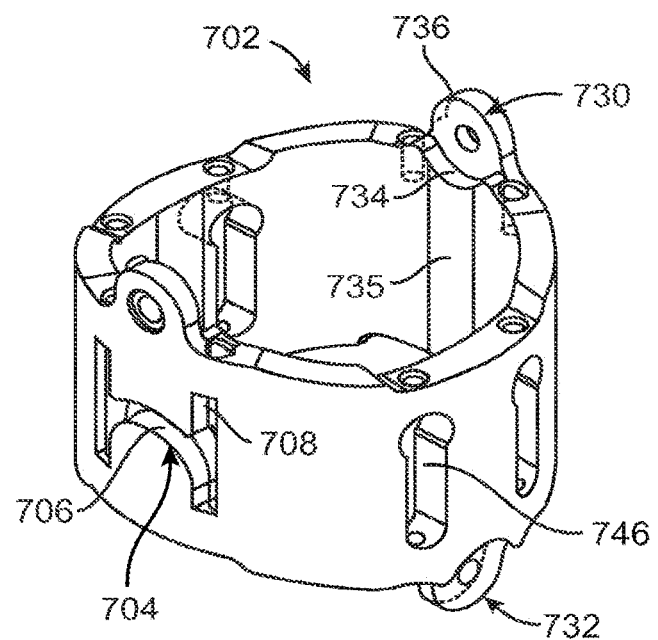
FIGS. 7a-7b are illustrations of a universal robotic link for use in an elongate robotic instrument.
Figure 7B:
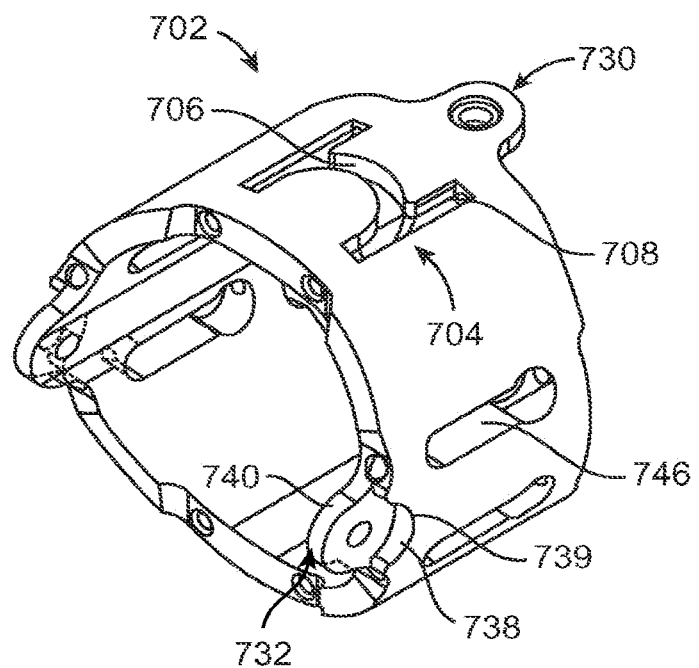

FIGS. 7a-7b illustrate one embodiment of a universal robotic link 702. In FIGS. 7a-7b, outer hinge portions 730, inner bearing surface 734, inner wall surface 735, outer ear 736, inner hinge portions 732, outer bearing surface 738, outer wall surface 739, and inner ear 740 can correspond, respectively, to outer hinge portions 330, inner bearing surface 334, inner wall surface 335, outer ear 336, inner hinge portions 332, outer bearing surface 338, outer wall surface 339, and inner ear 340 of FIG. 3.

Universal link 702 further includes integrated pulley and tendon guide 704, which has a pulley portion 706 and a tendon guide portion 708. The pulley portion can have a flat surface to reduce friction (the flat surface minimized contact area with a tendon passing over it), or alternatively the pulley portion can include a groove. The integrated pulley and tendon guide 704 combines the features of both the pulleys (e.g., pulley wheels 242 and pulley slots 243 in FIG. 2) and guide blocks or actuation tendon guides (e.g., guide blocks 444 in FIG. 4 or tendon guides 544 in FIG. 5) into a single component. Thus, each universal can provide for an actuation tendon wrapping around pulley portion 706 (e.g., similar in function to the front, middle, and back links described above in FIG. 2), or, alternatively, can be used as a intermediate link in which the actuation tendons pass through the lumens of the tendon guide portion 708 of each link.

In the embodiment of FIGS. 7a-7b, the integrated pulley and tendon guides 704 are positioned on the universal link in alignment with the outer hinge portions 732. Actuation tendon guides 746 can be positioned on the universal link in alignment with the inner hinge portions to provide lumens for which to route actuation tendons along the inner hinge portions as well. In other embodiments, the integrated pulley and tendon guides 704 can be positioned in alignment with the inner hinge portions and the tendon guides 746 can be positioned in alignment with the outer hinge portions, or alternatively, the integrated pulley and tendon guides 704 can be positioned in alignment with both the inner and outer hinge portions (e.g., four integrated pulley and tendon guides 704 per universal link).

The universal links described herein integrate all the features that are necessary for intermediate links and all the features that are needed in boundary links into a single link. Advantages of this design include: lower tooling costs (only one link is needed therefore only one tool needs to be made); the pulley has been integrated, and there is no bonding necessary of a separate pulley to the link; the pulley has a flat surface instead of a groove, which substantially reduces friction; the pulley has been implemented in such a way that derailing of the cable is very difficult due to the fact that the cable takes the shortest distance between lumens; even under compression/slack of the actuation tendons, the cables do not derail since they are guided and aligned by the lumens; and, all of the features have been implemented in such a way that the link can be manufactured by injection molding, which reduces the manufacturing cost substantially while maintaining the strength necessary for a robotic instrument.

Figure 8:
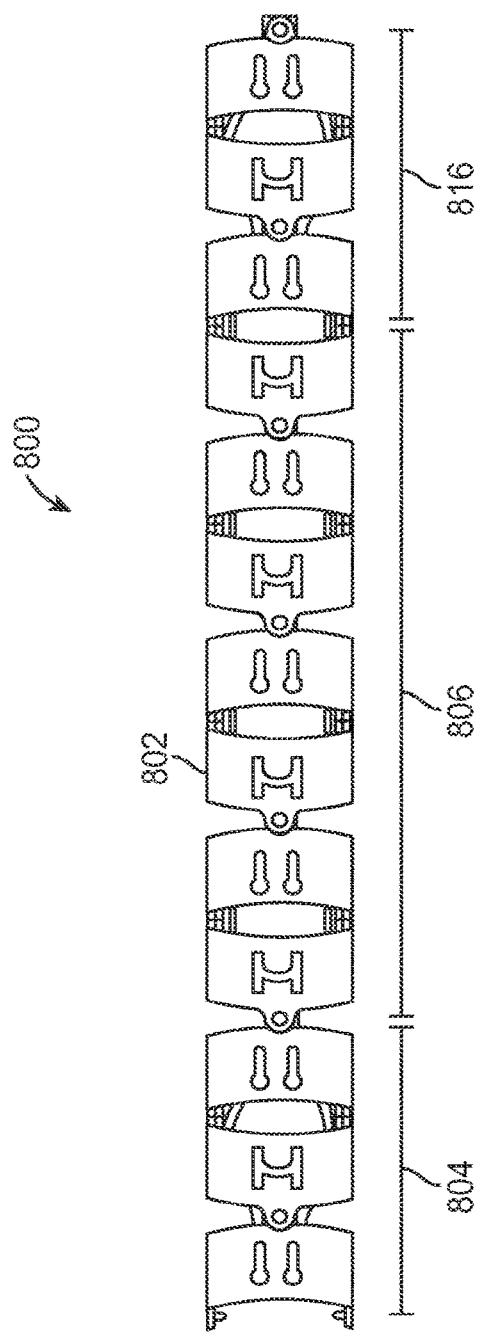
FIG. 8 illustrates an elongate robotic instrument comprising a plurality of universal links.

FIG. 8 is a side view of an elongate robotic instrument 800 comprising at least one universal link 802. The universal link 802 can correspond to the universal links 702 described above. The elongate robotic instrument can comprise any number of articulatable segments, depending on the desired length of the instrument, but a preferred embodiment includes four segments. Each segment can comprise a distal boundary portion 804, an intermediate portion 806, and a proximal boundary portion 816. As shown in FIG. 8, the boundary portions can include three universal links. The intermediate portion 806 can include any number of universal links, depending on the desired segment length and maximum desired angle of articulation. To utilize universal links in the distal boundary portion 804 of instrument 800, actuation tendons (not shown) can be attached to or routed around pulley portions integrated into the sidewall of the universal links. To utilize universal links in the intermediate portion 806, the actuation tendons can pass through the tendon guides integrated into the sidewall of the universal links, as described above with reference to FIG. 7.

Figure 9:
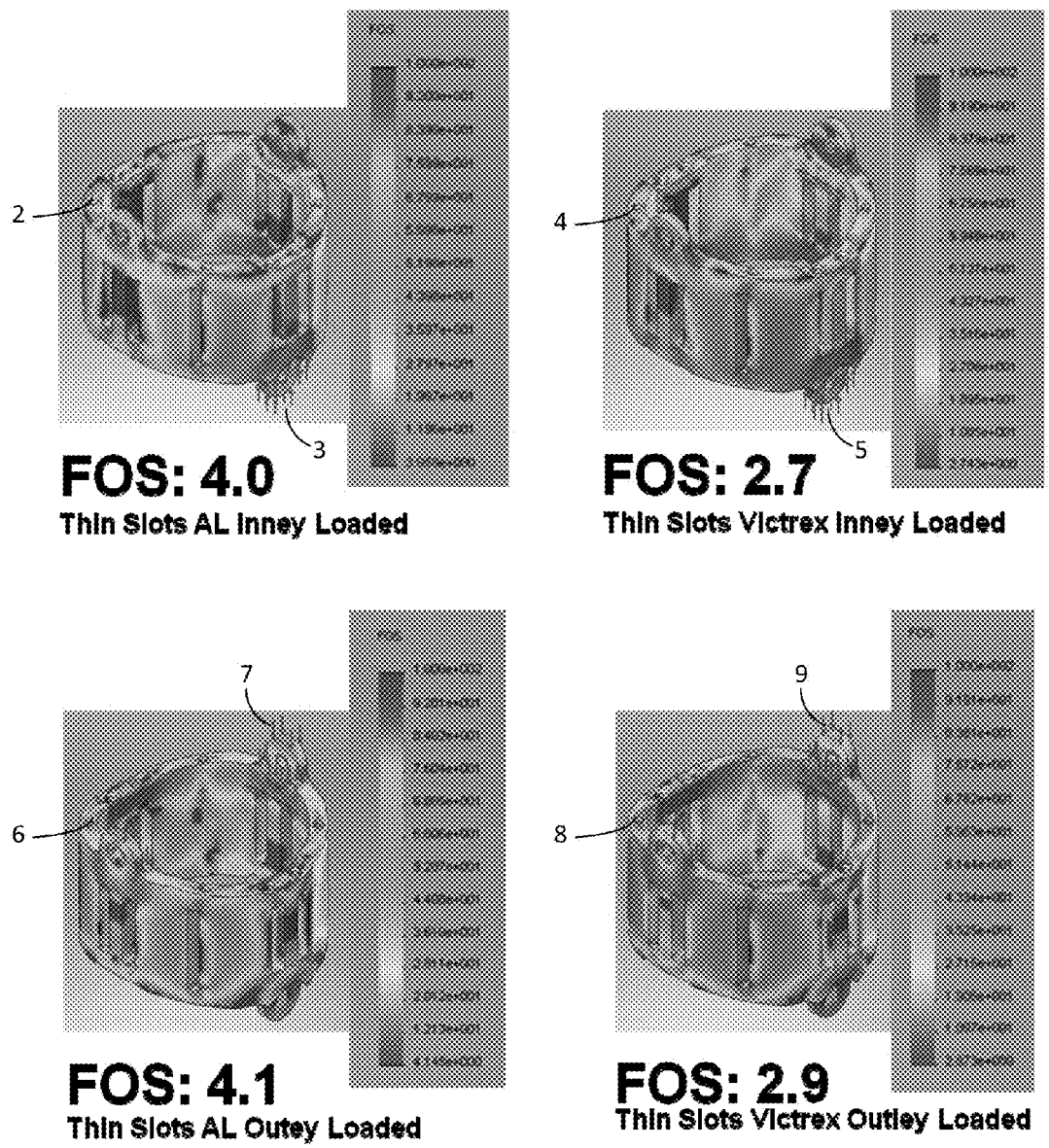
FIG. 9 shows a factor of safety for aluminum vs. victrex link designs.

FIG. 9 compares various embodiments of robotic link designs. Each robotic link illustrated has been subjected to forces to determine a factor of safety (FOS). A factor of safety is used here as an indicator of the relative strengths of different link designs. Referring to FIG. 9, link 2 is a robotic link made out of machined aluminum with a force applied to its inner hinge portions 3. Link 2 has a FOS of 4.0. Similarly, link 4 is a robotic link made out of injection molded plastic with a force applied to its inner hinge portions 5. Link 4 has a FOS of 2.7. Link 6 is a robotic link made out of machined aluminum with a force applied to its outer hinge portions 7. Link 6 has a FOS of 4.1. Similarly, link 8 is a robotic link made out of injection molded plastic with a force applied to its outer hinge portions 9. Link 8 has a FOS of 2.9.

Figure 10:
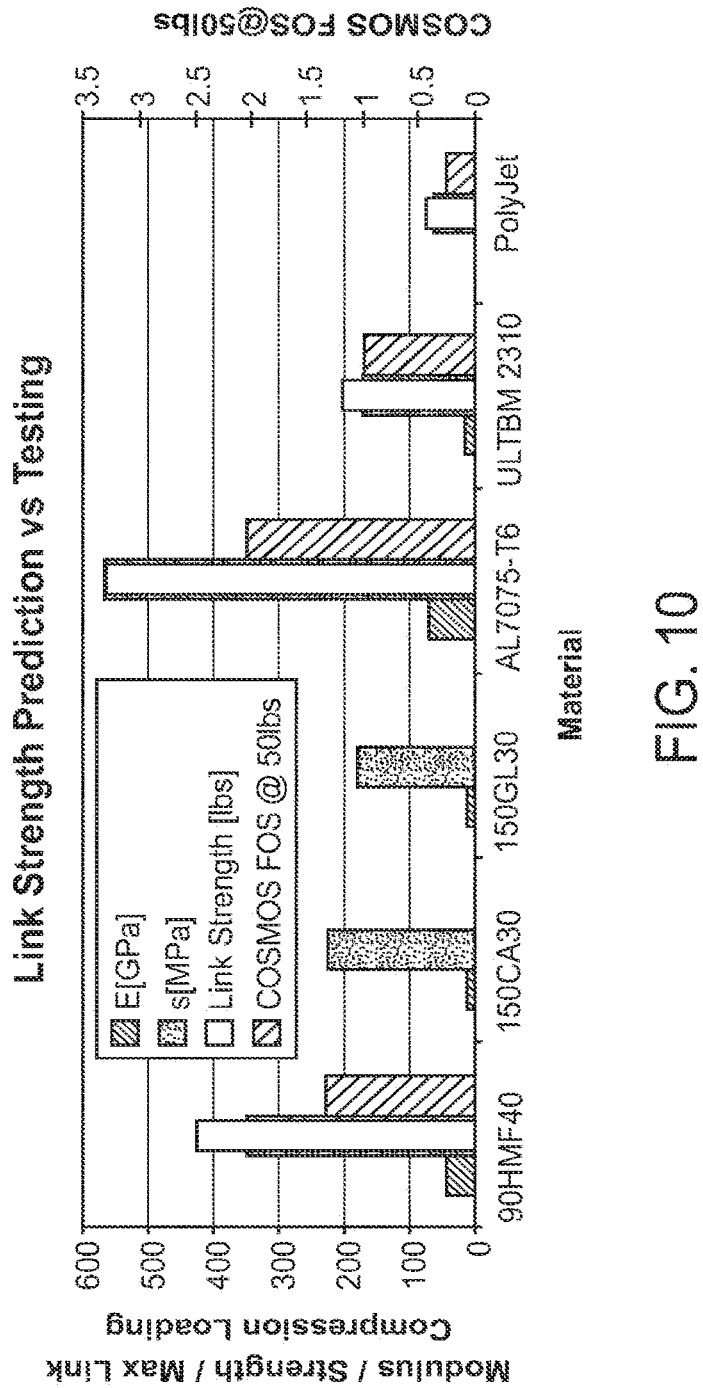
FIG. 10 is a bar graph illustrating predicted link strength vs. testing.

FIG. 10 is a chart comparing empirical data showing the strengths of various link designs and materials with theoretical data.

FIGS. 11a-11d illustrates various pie charts illustrating the effect of link diameter and the use of guide blocks on the internal volume available in a robotic instrument. FIG. 11a illustrates internal volume usage of a robotic instrument comprising robotic links with a 0.75-inch outer diameter and utilizing guide blocks. FIG. 11b illustrates the internal volume usage of a robotic instrument comprising robotic links with a 0.7-inch outer diameter and utilizing guide blocks. FIG. 11c illustrates internal volume usage of a robotic instrument comprising robotic links with a 0.75 inch outer diameter and no guide blocks (e.g., integrated tendon guides). FIG. 11d illustrates the internal volume usage of a robotic instrument comprising robotic links with a 0.7-inch outer diameter and no guide blocks (e.g., integrated tendon guides).

Figure 12:
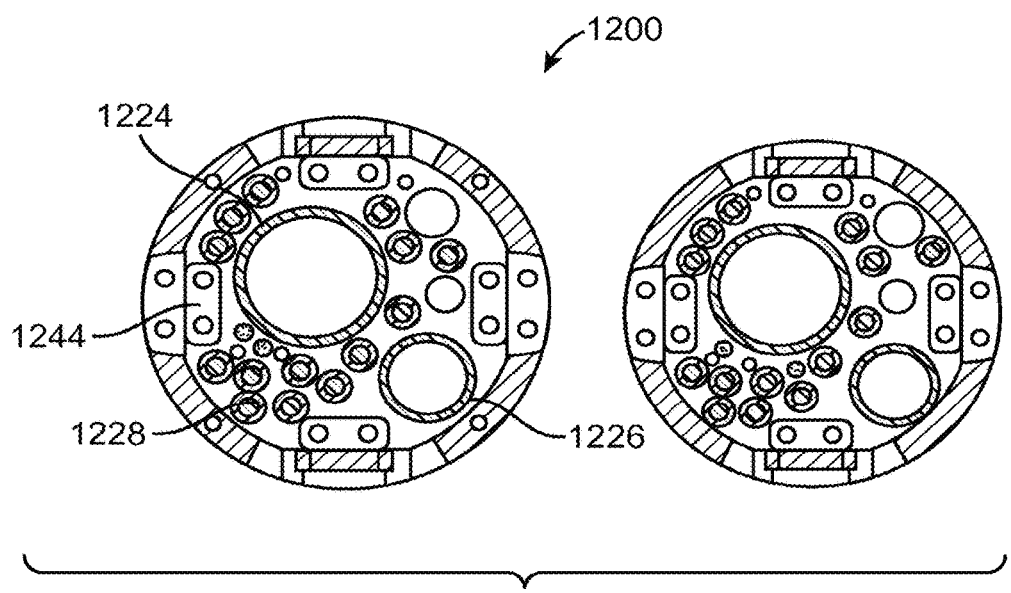
FIG. 12 is a cross sectional view of links with guide blocks.
Figure 13:
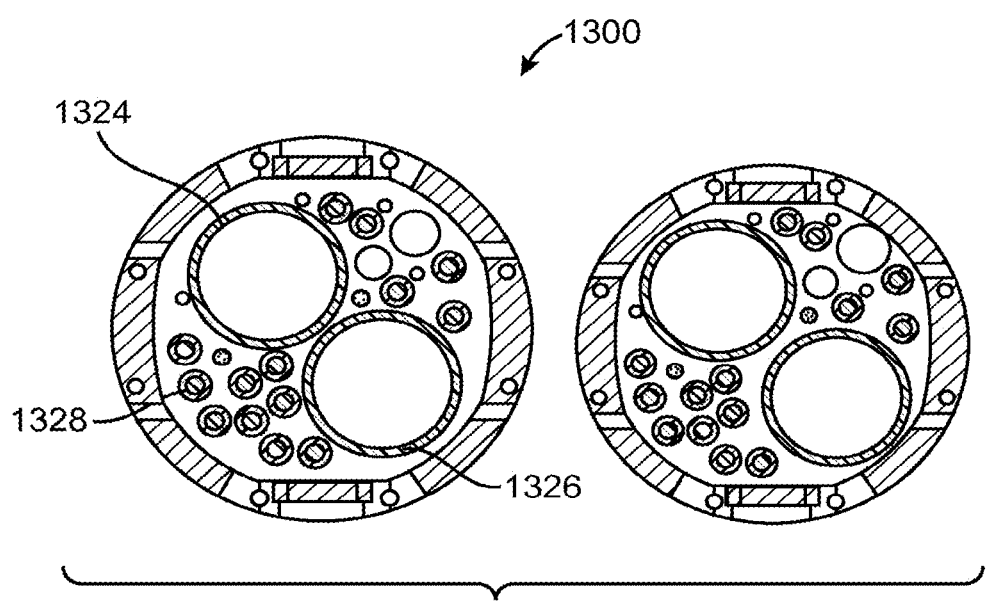
FIG. 13 is a cross sectional view of links without guide blocks.

FIG. 12 is a cross sectional view of a robotic instrument 1200, showing the internal volume of a link when the link utilizes guide blocks 1244. FIG. 12 further illustrates working channels 1224 and 1226 and actuation tendons 1228. FIG. 13 is a cross sectional view of a robotic instrument 1300, showing the internal volume of a link when the link does not utilize external guide blocks. Rather, the instrument of FIG. 13 can use integrated tendon guides, as described above. It can be easily seen that the embodiment shown in FIG. 13 reserves a larger volume of the interior cavity of the robotic instrument for working channels 1324 and 1326 and actuation tendons 1328.

Aspects of various embodiments include: dimensioning and design of the part to make it mass-manufacturable by injection molding while still withstanding the high compressive loading that occurs inside robotic endoscopes; double knee-joint to resolve compressive loading during articulation, integrated static pulley; flat pulley surface to reduce friction; and, integrated design of cable routing features that allows the same part to be used as a segment boundary and passive link.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method comprising:
    articulating a first link and a second link relative to each other about a pair of outer hinge portions on a first end of the first link and in mating engagement with a pair of inner hinge portions on a second end of the second link;
    wherein each outer hinge portion comprises an outer ear extending in a first axial direction away from the first end of the first link, and an inner bearing surface substantially oriented in the first axial direction;
    wherein each inner hinge portion comprises an inner ear extending in a second axial direction away from the second end of the second link, and an outer bearing surface positioned oriented in the second axial direction;
    wherein, during the articulating, the outer bearing surfaces support the outer ears and the inner bearing surfaces support the inner ears.

2. The method of claim 1, wherein each of the pair of outer hinge portions are diametrically opposed across the first link.

3. The method of claim 1, wherein each of the pair of inner hinge portions are diametrically opposed across the second link.

4. The method of claim 1, further comprising articulating the second link and a third link relative to each other about a pair of outer hinge portions on a first end of the second link in mating engagement with a pair of inner hinge portions on a second end of the third link.

5. The method of claim 4, wherein:
    articulating the first link and the second link relative to each other comprises articulating the first link and the second link relative to each other about a first axis of rotation, and
    wherein articulating the second link and the third link relative to each other comprises articulating the second link and the third link relative to each other about a second axis of rotation perpendicular to the first axis of rotation.

6. The method of claim 1, wherein articulating the first link and the second link relative to each other comprises sliding inner surfaces of the outer ears against outer surfaces of the inner ears.

7. The method of claim 1, wherein articulating the first link and the second link relative to each other comprises sliding the outer ears against the outer bearing surfaces and sliding the inner ears against the inner bearing surfaces.

8. The method of claim 1, wherein articulating the first link and the second link relative to each other comprises articulating the first link and the second link relative to each other by applying an actuation force to at least one of the first link and the second link.

9. The method of claim 8, wherein applying an actuation force to at least one of the first link and the second link comprises tensioning an actuation tendon connected to at least one of the first link and the second link.

10. The method of claim 9, wherein applying the actuation force to the at least one of the first link and the second link comprises tensioning the actuation tendon on a first side of a pulley coupled with at least one of the first link and the second link and around which the actuation tendon is at least partially wrapped and slackening the actuation tendon on a second side of the pulley.

11. The method of claim 9, wherein tensioning the actuation tendon comprises drawing the tendon through a guide block positioned proximate at least one inner hinge portion of the pair of inner hinge portions.

12. The method of claim 9, wherein tensioning the actuation tendon comprises drawing the tendon through a coil tube connected to one of the first and second links.

13. The method of claim 1, wherein articulating the first link and the second link relative to each other comprises articulating the first link and the second link relative to each other through an angular range of +/−30 degrees.

14. A method of assembling an elongated instrument, comprising:
   positioning a pair of outer hinge portions of a first end of a first link in mating engagement with a pair of inner hinge portions of a second end of a second link;
   wherein positioning the pair of outer hinge portions in mating engagement with the pair of inner hinge portions comprises:
      placing an outer ear of the outer hinge portion in sliding engagement with an outer bearing surface of the inner hinge portion, and
      placing an inner ear of the inner hinge portion in sliding engagement with an inner bearing surface of the outer hinge portion.

15. The method of claim 14, wherein positioning the pair of outer hinge portions in mating engagement with the pair of inner hinge portions comprises placing an inner surface of the outer ear in sliding contact with an outer surface of the inner ear.

16. The method of claim 14, further comprising connecting one or more actuation tendons to a respective one or more of the first link and the second link.

17. The method of claim 14, further comprising routing at least one actuation tendon through a passage formed in at least one of the first link and the second link.

18. The method of claim 14, further comprising routing at least one actuation tendon through a coil tube extending through a passage formed in at least one of the first link and the second link.

19. The method of claim 14, further comprising routing at least one actuation tendon through a passage formed in one or more guide blocks each connected to a respective one of the first link and the second link.

20. The method of claim 14, further comprising placing an imaging device in a lumen extending longitudinally through the first link and the second link.

* * * * *